United States Patent
Boucher, Jr. et al.

[11] Patent Number: 5,876,700
[45] Date of Patent: Mar. 2, 1999

[54] METHODS OF HYDRATING LUNG MUCOUS SECRETIONS WITH BENZAMIL OR PHENAMIL

[75] Inventors: Richard C. Boucher, Jr.; Monroe Jackson Stutts, both of Chapel Hill, N.C.

[73] Assignee: The University of North Carolina at Chapel Hill, Chapel Hill, N.C.

[21] Appl. No.: 792,887

[22] Filed: Jan. 31, 1997

Related U.S. Application Data

[63] Continuation-in-part of Ser. No. 355,650, Dec. 14, 1994, Pat. No. 5,656,256.

[51] Int. Cl.$^6$ .................................................. A61K 9/12
[52] U.S. Cl. ............................. 424/45; 424/46; 514/851
[58] Field of Search ..................... 424/45, 46; 514/851

[56] References Cited

U.S. PATENT DOCUMENTS

| | | | |
|---|---|---|---|
| 3,313,813 | 4/1967 | Cragoe, Jr. et al. | 514/51 |
| 4,501,729 | 2/1985 | Boucher et al. | 424/45 |
| 5,292,498 | 3/1994 | Boucher, Jr. | 424/45 |
| 5,304,125 | 4/1994 | Leith | 604/57 |
| 5,512,269 | 4/1996 | Uedia et al. | 424/45 |
| 5,635,160 | 6/1997 | Stutts, III et al. | 424/45 |
| 5,656,256 | 8/1997 | Boucher et al. | 424/45 |

FOREIGN PATENT DOCUMENTS 0 451 130   10/1991   European Pat. Off. .

OTHER PUBLICATIONS

M. R. Knowles, et al; *Activation by Extracellular Nucleotides of Chloride Secretion in the Airway Epithelia of Patients with Cystic Fibrosis*, N Engl J Med 325, pp. 533–538 (1991).

S.J. Mason et al; *Regulation of transepithelial ion transport and intracellular calcium by extracellular ATP in human normal and cystic fibrosis airway epithelium*, Br. J. Pharmacol. 103, pp. 1649–1656 (1991).

N.J. Willumsen and R.C. Boucher; *Sodium transport and intracellular sodium activity in cultured human nasal epithelium*, Am. J. Physiol. (Cell Physiol 25) 256 C1033–C1053 (1989).

*Primary Examiner*—Raj Bawa
*Attorney, Agent, or Firm*—Myers Bigel Sibley & Sajovec

[57] ABSTRACT

Methods of hydrating lung mucous secretions in the lungs of a subject are disclosed. The methods involve administering benzamil or phenamil to the lungs of the subject in an amount effective to hydrate lung mucous secretions. The administering step is preferably carried out by inhalation administration. The method is useful in the treatment of diseases such as cystic fibrosis and chronic bronchitis.

22 Claims, 2 Drawing Sheets

METHODS OF HYDRATING LUNG MUCOUS SECRETIONS WITH BENZAMIL OR PHENAMIL

RELATED APPLICATIONS

This application is a continuation-in-part of U.S. patent application Ser. No. 08/355,650, filed 14 Dec. 1994, now U.S. Pat. No. 5,656,256, issued 12 Aug. 1997.

FEDERALLY SUPPORTED RESEARCH

These inventions were made with Government support under grant number 22924 from the National Institutes of Health (NIH) Heart and Lung Institute. The Government has certain rights to these inventions.

FIELD OF THE INVENTION

These inventions relate to a method of hydrating lung mucous secretions by administering benzamil to the lungs of a subject, and a method of hydrating lung mucous secretions by administering phenamil to the lungs of a subject.

BACKGROUND OF THE INVENTION

In cystic fibrosis several functions of airway epithelia are abnormal, and deficiencies in both $Cl^-$ transport and $Na^+$ absorption are well documented. See, e.g. Knowles et al., *Science* 221, 1067 (1983); Knowles et al., *J. Clin. Invest.* 71, 1410 (1983). Regulation of ion transport might have potential therapeutic benefit in lung diseases characterized by abnormalities in epithelial ion transport, e.g., cystic fibrosis.

One therapeutic goal in cystic fibrosis and other pulmonary diseases in which the water content of the mucous is altered is to hydrate the lung mucous secretions, so that the secretions may be thereafter more easily removed from the lungs by mucociliary action or simple coughing. The use of aerosolized amiloride to hydrate mucous secretions is described in U.S. Pat. No. 4,501,729 to Boucher et al. Amiloride appears to block $Na^+$ reabsorption by airway epithelial cells, and therefore inhibits water absorption from the mucous. While an important breakthrough in providing treatments for cystic fibrosis, a potential problem with amiloride treatments is the relatively short duration of action of amiloride.

A different therapeutic approach for hydrating lung mucous secretions is exemplified by techniques that involve the administration of ATP or UTP, which appear to stimulate chloride secretion from respiratory epithelial cells. See, e.g., U.S. Pat. No. 5,292,498 to Boucher.

In view of the large numbers of people afflicted with cystic fibrosis, there is an ongoing need for new methods for providing methods of hydrating lung mucous secretions and thereby facilitating lung mucous clearance.

SUMMARY OF THE INVENTION

A first aspect of the present invention is a method of hydrating mucous secretions in the lungs of a subject in need of such treatment. The method comprises administering benzamil to the lungs of the subject in an amount effective to hydrate lung mucous secretions.

A second aspect of the present invention is a method of treating cystic fibrosis in a human subject in need of such treatment, comprising administering by inhalation an aerosol suspension of respirable particles to the respiratory system of the subject, the particles comprised of benzamil, the benzamil administered in an amount effective to hydrate retained lung mucous secretions in the lungs of the subject, whereby the retained mucous secretions are more easily transported from the lungs via mucociliary action.

A third aspect of the present invention is the use of benzamil for the manufacture of a medicament for carrying out a therapeutic method of treatment as given above.

A fourth aspect of the present invention is a pharmaceutical composition, comprising, together in a pharmaceutically acceptable carrier, (i) benzamil in an amount effective to inhibit the reabsorption of water from lung mucous secretions; and (ii) UTP or an analog thereof in an amount effective to hydrate lung mucous secretions.

A fifth aspect of the present invention is a method of hydrating mucous secretions in the lungs of a subject in need of such treatment. The method comprises administering phenamil to the lungs of the subject in an amount effective to hydrate lung mucous secretions.

A sixth aspect of the present invention is a method of treating cystic fibrosis in a human subject in need of such treatment, comprising administering by inhalation an aerosol suspension of respirable particles to the respiratory system of the subject, the particles comprised of phenamil, the phenamil administered in an amount effective to hydrate retained lung mucous secretions in the lungs of the subject, whereby the retained mucous secretions are more easily transported from the lungs via mucociliary action.

A seventh aspect of the present invention is the use of phenamil for the manufacture of a medicament for carrying out a therapeutic method of treatment as given above.

An eighth aspect of the present invention is a pharmaceutical composition, comprising, together in a pharmaceutically acceptable carrier, (i) phenamil in an amount effective to inhibit the reabsorption of water from lung mucous secretions; and (ii) UTP or an analog thereof in an amount effective to hydrate lung mucous secretions.

DETAILED DESCRIPTION OF THE INVENTION

Figure 1:
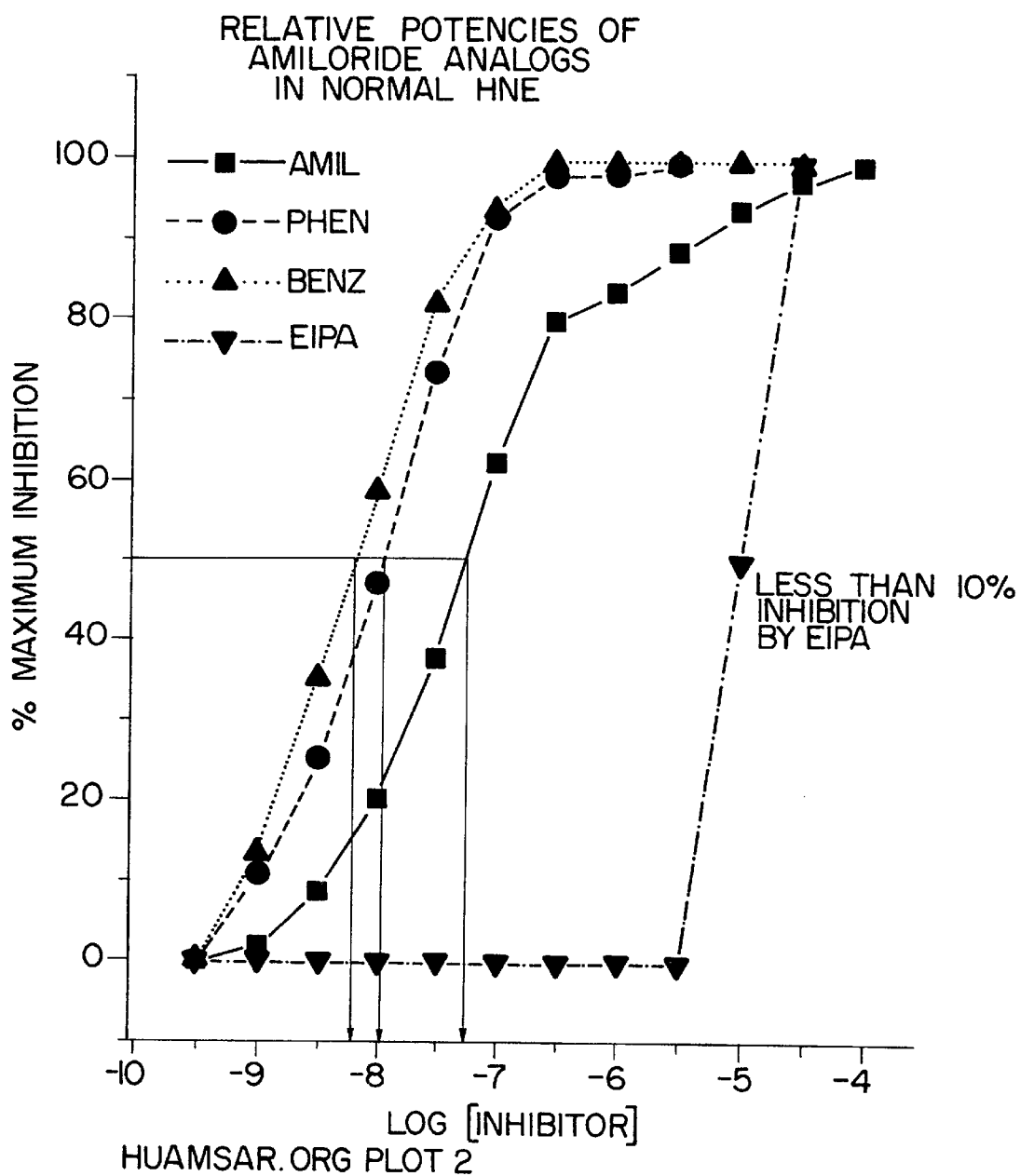
FIG. 1 shows the log concentration-effect curves (percentage change in $I_{sc}$ from basal levels) of amiloride, benzamil, phenamil and 5-(N,N,-hexamethylene)amiloride (or EIPA) applied to the apical surface of human nasal epithelium.

The method of the present invention may be used to remove mucous secretions retained in the lungs of a subject for any reason, including (but not limited to) retention of secretions arising from airway diseases such as cystic fibrosis, chronic bronchitis, asthma, and bronchiectasis. Two compounds, phenamil and benzamil, were identified as particularly potent blockers of airway epithelial $Na^+$ channels, having $K_i$'s of $<10^{-7}$ M in human airway epithelial preparations. The novel features of benzamil and phenamil as compared to amiloride are that these compounds are 1–1.5 log-concentration units more potent than amiloride. Additionally, they appear to bind more avidly to the $Na^+$ channel and thus have longer durations of action during intermittent dose regimens.

The method of the present invention can be used to facilitate (i.e., enhance, speed, assist) the clearance of mucous secretions from the lungs of a subject in need of such treatment for any reason, including (but not limited to) retained secretions arising from airway diseases such as cystic fibrosis, chronic bronchitis, asthma, bronchiectasis, post-operative atelectasis (plugging of airways with retained secretions after surgery), and Kartagener's syndrome.

The present invention is concerned primarily with the treatment of human subjects, but may also be employed for the treatment of other mammalian subjects, such as dogs and cats, for veterinary purposes.

Benzamil (also known as 3,5-diamino-6-chloro-N-(benzylaminoaminomethylene)pyrazinecarboxamide) and phenamil (also known as 3,5-diamino-6-chloro-N-(phenylaminoaminomethylene)pyrazinecarboxamide) are known compounds and are disclosed in U.S. Pat. No. 3,313,813 to E. Cragoe (applicant specifically intends that the disclosure of this and all other patents cited herein be incorporated herein by reference).

The terms "benzamil" and "phenamil" as used herein, include the pharmaceutically acceptable salts thereof, such as (but not limited to) benzamil hydrochloride or phenamil hydrochloride. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Benzamil or phenamil used to prepare compositions for the present invention may alternatively be in the form of a pharmaceutically acceptable free base of benzamil or phenamil. Because the free base of the compound is less soluble than the salt, free base compositions are employed to provide more sustained release of benzamil or phenamil to the lungs. Benzamil or phenamil present in the lungs in particulate form which has not gone into solution is not available to induce a physiological response, but serves as a depot of bioavailable drug which gradually goes into solution.

The active compounds disclosed herein may be administered to the lungs of a patient by any suitable means, but are preferably administered by administering an aerosol suspension of respirable particles comprised of the active compound, which the subject inhales. The active compound can be aerosolized in a variety of forms, such as, but not limited to, dry powder inhalants, metered dose inhalants, or liquid/liquid suspensions. The respirable particles may be liquid or solid.

In one embodiment of the invention, the particulate benzamil or phenamil composition may contain both a free base of phenamil or benzamil and a pharmaceutically acceptable salt such as benzamil hydrochloride or phenamil hydrochloride to provide both early release of and sustained release of benzamil or phenamil for dissolution into the mucous secretions of the lungs. Such a composition serves to provide both early relief to the patient, and sustained relief over time. Sustained relief, by decreasing the number of daily administrations required, is expected to increase patient compliance with a course of benzamil or phenamil treatments.

Solid or liquid particulate benzamil or phenamil prepared for practicing the present invention should include particles of respirable size: that is, particles of a size sufficiently small to pass through the mouth or nose and larynx upon inhalation and into the bronchi and alveoli of the lungs. In general, particles ranging from about 1 to 5 microns in size (more particularly, less than about 4.7 microns in size) are respirable. Particles of non-respirable size which are included in the aerosol tend to be deposited in the throat and swallowed, and the quantity of non-respirable particles in the aerosol is preferably minimized. For nasal administration, a particle size in the range of 10–500 $\mu$m is preferred to ensure retention in the nasal cavity.

The dosage of the active compound, or the pharmaceutically acceptable salt thereof, will vary depending on the condition being treated and the state of the subject, but generally may be an amount sufficient to achieve dissolved concentrations of active compound on the airway surfaces of the subject of from about $10^{-9}$ to about $10^{-2}$ Moles/liter or even $10^{-1}$ Moles/liter, more preferably from about $10^{-5}$ to about $10^{-1}$ Moles/liter, and most preferably from about $10^{-4}$ to about $10^{-3}$ to about $10^{-1}$ moles/liter. Depending upon the solubility of the particular formulation of active compound administered, the daily dose may be divided among one or several unit dose administrations. The daily dose by weight may range, for example, from about 1 to 20 milligrams of respirable benzamil or phenamil particles for a human subject, depending upon the age and condition of the subject. A currently preferred unit dose is about 2 milligrams of respirable benzamil or phenamil particles given at a regimen of four administrations per day. The dosage may be provided as a prepackaged unit by any suitable means (e.g., encapsulating in a gelatin capsule).

In the manufacture of a formulation according to the invention, active agents or the pharmaceutially acceptable salts or free bases thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a capsule, which may contain from 0.5% to 99% by weight of the active compound. One or more active compounds may be incorporated in the formulations of the invention, which formulations may be prepared by any of the well-known techniques of pharmacy consisting essentially of admixing the components.

Aerosols of liquid particles comprising the active compound may be produced by any suitable means, such as with a pressure-driven jet aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, and is preferably made isotonic (but may be hypertonic) with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 200 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

Any propellant may be used in carrying out the present invention, including both chlorofluorocarbon-containing propellants and non-chlorofluorocarbon-containing propellants. Thus, fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3—CHF—CF_2H$; $CF_3—CH_2—CF_2H$; $CF_3—CHF—CF_3$; $CF_3—CH_2—CF_3$; $CF_3—CHCl—CF_2Cl$; $CF_3—CHCl—CF_3$; cy—$C(CF_2)_3—CHCl$; $CF_3—CHCl—CH_2Cl$; $CF_3—CHF—CF_2Cl$; $CF_3—CHCl—CFHCl$; $CF_3—CFCl—CFHCl$; $CF_3—CF_2—CF_2H$; $CF_3—CF_2—CH_3$; $CF_2H—CF^2—CFH_2$; $CF_3—CF_2—CFH_2$; $CF_3—CF_2—CH_2Cl$; $CF_2H—CF_2—CH_2$; $CF_2H—CF_2—CH_2Cl$; $CF_3—CF_2—CF_2—CH_3$; $CF_3—CF_2—CF_2—CF_2H$; $CF_3—CHF—CHF—CF_3$; $CF_3—O—CF_3$; $CF_3—O—CF_2H$; $CF_2H—H—O—CF_2H$; $CF_2H—O—CFH_2$; $CF_3—O—CH_3$; $CF_3—O—CF_2—CF_2H$; $CF_3—O—CF_2—O—CF_3$; cy—$CF_2—CF_2—O—CF_2$—; cy—$CHF—CF_2—O—CF_2$—; cy—$CH_2—CF_2—O—CF_2$—; cy—$CF_2—O—CF_2—O—CF_2$—; $CF_3—O—CF_2—Br$; $CF_2H—O—CF_2—Br$; and mixtures thereof, where "cy" denotes a cyclic compound in which the end terminal covalent bonds of the structures shown are the same so that the end terminal groups are covalently bonded together. Particularly preferred are hydrofluoroalkanes such as 1,1,1,2-tetrafluoroethane (propellant 134a) and heptafluoropropane (propellant 227). A stabilizer such as a fluoropolymer may optionally be included in formulations of fluorocarbon propellants, such as described in U.S. Pat. No. 5,376,359 to Johnson.

Compositions containing respirable dry particles of micronized benzamil or phenamil may be prepared by grinding the dry phenamil or benzamil with a mortar and pestle, and then passing the micronized composition through a 400 mesh screen to break up or separate out large agglomerates. The active compound may be formulated alone (i.e., the solid particulate composition may consist essentially of the active compound) or in combination with a dispersant, diluent or carrier, such as sugars (i.e., lactose, sucrose, trehalose, mannitol) or other acceptable excipients for lung or airway delivery, which may be blended with the active compound in any suitable ratio (e.g., a 1 to 1 ratio by weight). The dry powder solid particulate composition may be obtained by methods known in the art, such as spray-drying, milling, freeze-drying, etc.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

If desired, the benzamil or phenamil may be concurrently administered with uridine 5'-triphosphate (UTP) or an analog thereof (including the pharmaceutically acceptable salts thereof) in an amount effective to stimulate chloride secretion from respiratory epithelial cells (thereby further hydrating the lung mucous secretions) and/or stimulate ciliary beat frequency. Pharmaceutical formulations containing benzamil or phenamil may also contain UTP or an analog thereof in an amount effective to stimulate chloride secretion from respiratory epithelial cells and/or stimulate ciliary beat frequency. UTP and analogs thereof that may be used to carry out this technique are disclosed in U.S. Pat. No. 5,292,498 to Boucher. In general, such compounds are of the structure of Formula (I) below, or a pharmaceutically acceptable salt (as given above) thereof:

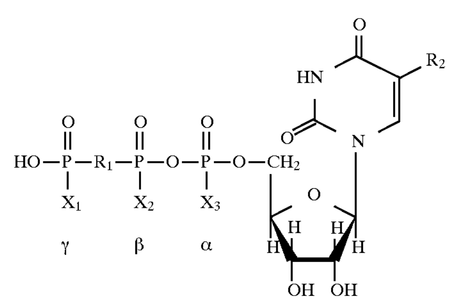

(I)

wherein:

$X_1$, $X_2$, and $X_3$ are each independently either $O^-$ (i.e., OH) or $S^-$ (i.e., SH). Preferably $X_2$ and $X_3$ are $O^-$.

$R_1$ is O, imido, methylene, dihalomethylene (e.g., dichloromethylene, difluoromethylene). Preferably, $R_1$ is oxygen.

$R_2$ is H or Br. Preferably, $R_2$ is H.

A particularly preferred compound of Formula (I) above is the UTP analog uridine 5'—O—(3-thiotriphosphate) (or "UTPγS"). The active compounds of Formula (I) may be administered by themselves or in the form of their pharmaceutically acceptable salts, e.g., an alkali metal salt such as sodium or potassium, an alkaline earth metal salt, or an ammonium and tetraalkyl ammonium salt, $NX_4^+$ (wherein X is a $C_{1-4}$ alkyl group).

The present invention is explained in greater detail in the Examples which follow. These examples are intended as illustrative of the invention, and are not to be taken as limiting thereof. Amiloride was obtained from Sigma Chemicals (St. Louis, Mo.); benzamil and phenamil were a gift from Dr. Thomas Kleyman of the University of Pennsylvania. The composition of Krebs bicarbonate Ringer's solution (KBR) was 140 milliMolar (mM) $Na^+$, 120 mM $Cl^-$, 5.2 mM $K^+$, 25 mM $HCO_3^-$, 2.4 mM $HPO_4^{2-}$, 0.4 mM $H_2PO_4^-$, 1.1 mM $Ca^{2+}$, and 5 mM glucose.

EXAMPLE 1

Human Nasal Epithelium (HNE) Cultures

Nasal specimens are obtained from human subjects and are typically inferior turbinates removed for sleep apnea syndromes or plastic reconstruction. The cell culture procedures used in this example are performed as described in Willumsen, N. J., et al., *Am. J. Physiol.* 256:C1033–C1044 (*Cell. Physiol.* 25) (1989) and Yankaskas, J. R., et al., *Am. Rev. Respir. Dis.* 132:1281–1287 (1985). Cells from freshly excised specimens are protease isolated with protease XIV (Sigma, St, Louis, Mo.), concentrated, and plated on collagen membranes in the bottom of plastic-tissue culture cups. The cells are fed for 5 days with serum-free F-12 medium containing the following additives (F-12/7X): insulin, epidermal growth factor, cholera toxin, transferrin, hydrocortisone, triiodothyronine, and endothelial cell growth substance. Subsequently, they are fed with F-12/7X media supplemented (1:1) with 3T3 fibroblast-conditioned media containing 1% fetal bovine serum. After the fifth day in culture, the transepithelial potential difference (PD) developed by the culture is measured daily to detect the occurrence of confluency. Cell preparations are routinely studied within 1 day of the development of the maximal PD.

EXAMPLE 2

Electrophysiological Measurements

The transepithelial electrophysiological techniques used in this example have been described in Willumsen, N. J., et al., *Am. J. Physiol.* (*Cell Physiol.* 25) 256:C1033–C1053 (1989).

The tissue preparation described in Example 1 is mounted in a modified (superfusion, not recirculating), miniature Ussing chamber interfaced to a voltage clamp that measures transepithelial PD and the PD response to constant current (I) pulses. The chamber contains 1 ml of bathing solution for each (apical; basolateral) surface of the preparation. The solution used as the vehicle for drug delivery is a Krebs bicarbonate Ringer solution (KBR) which approximates the ionic composition of plasma. This solution is warmed (37°) and gassed (95% oxygen, 5% $CO_2$) to maintain pH 7.4. The cultured cells are superfused on both surfaces with KBR. Drugs are delivered by adding drug selectively to the apical or basolateral perfusate and monitoring the preparation for 5 minutes with a drug expected to affect transepithelial sodium transport (here, amiloride, benzamil, phenamil or 5-(N,N,-hexamethylene)amiloride (EIPA)).

The measurement of sodium transport rates is performed by recording the spontaneous transepithelial PD ($V_t$) and responses of the PD to constant current pulses. From the relationship between $V_t$ and induced $V_t$ deflections, the transepithelial resistance ($R_t$) is calculated. The short-circuit current ($I_{sc}$), or measure of sodium transport rate, is determined as $I_{sc}=V_t/R_t$. Measurements of transepithelial unidirectional isotopic Na+ fluxes, in cultures matched on the basis of $V_t$ and $R_t$ (<25% difference), mounted in Ussing chambers, bathed by KBR, gassed with a 95% $O_2$–5% $CO_2$ gas mixture, and warmed to 37° C., confirmed that $I_{sc}$ is a measure of $Na^+$ transport.

Each cultured human airway epithelial preparation is exposed to different concentrations ($10^{-8}M$–$10^{-3}M$) of a sodium-channel blocking drug on either the basolateral or apical surface for the dose response studies. To construct concentration-effect relationships of the response to the drugs, it was assumed that the same maximum response to a drug could be induced from each tissue culture preparation from the same individual.

EXAMPLE 3

Comparative Example A

Effects of Benzamil and Phenamil on Sodium Absorption as Compared with Amiloride FIG. 1 shows the log concentration-effect curves (percentage of maximum inhibition of sodium absorption as a function of the log of drug concentration) of amiloride, benzamil, phenamil and 5-(N,N,-hexamethylene)amiloride (or EIPA) applied to the apical surface of human nasal epithelium. Data points represented by inverted triangles indicate the effect of EIPA on sodium absorption; upright triangles indicate benzamil; circles represent phenamil and squares represent amiloride.

These results illustrate the comparative effects of amiloride, benzamil and phenamil on the steady-state inhibition of $Na^+$ transport rates by human nasal epithelia. Sodium uptake is inhibited less than 10% by EIPA; that is, EIPA has very little effect on sodium transport rate. Amiloride appears to be a potent blocker of apical $Na^+$ channels in $Na^+$-absorbing epithelia, but is significantly less potent than benzamil or phenamil, which achieve the same level of complete sodium channel blocking at approximately one log concentration less.

EXAMPLE 4

Comparative Example B

Persistence of Efficacy of Benzamil Phenamil and Amiloride

In vivo, drug is delivered to the lungs as a single bolus. Hence, the duration of drug action in vivo will reflect (1) the retention of the drug in the airway surface liquid compartment, and (2) binding of drug to the target site within the airway epithelium. This Example illustrates the contribution of binding of drug to the target site (2) to the duration of drug action.

A protocol was designed to measure the duration of drug action after removal of drug from the airway surface liquid compartment. For this protocol, human airway epithelial preparations as described in Example 1 are mounted in modified Ussing chambers and interfaced to voltage clamps as described above in Example 2. Basal measurements of $I_{sc}$ in KBR are made and the steady state response to a 5 minute administration of a single maximal effective concentration ($10^{-5}M$) of drug delivered to the luminal surface is measured. Following this step, administration of the drug is stopped, the lumen is perfused with standard KBR solutions, and the time required for $I_{sc}$ to return to baseline or basal levels is measured. The percent washout time for each drug is calculated as:

$$\frac{T_{rbX} - T_{cdX}}{T_{rbA} - T_{cdA}} \times 100$$

where $T_{rb}$=time to return to basal $I_{sc}$ after cessation of drug administration; $T_{cd}$=time at which administration of drug ceases; X=test drug (benzamil or phenamil); and A=amiloride.

Figure 2:
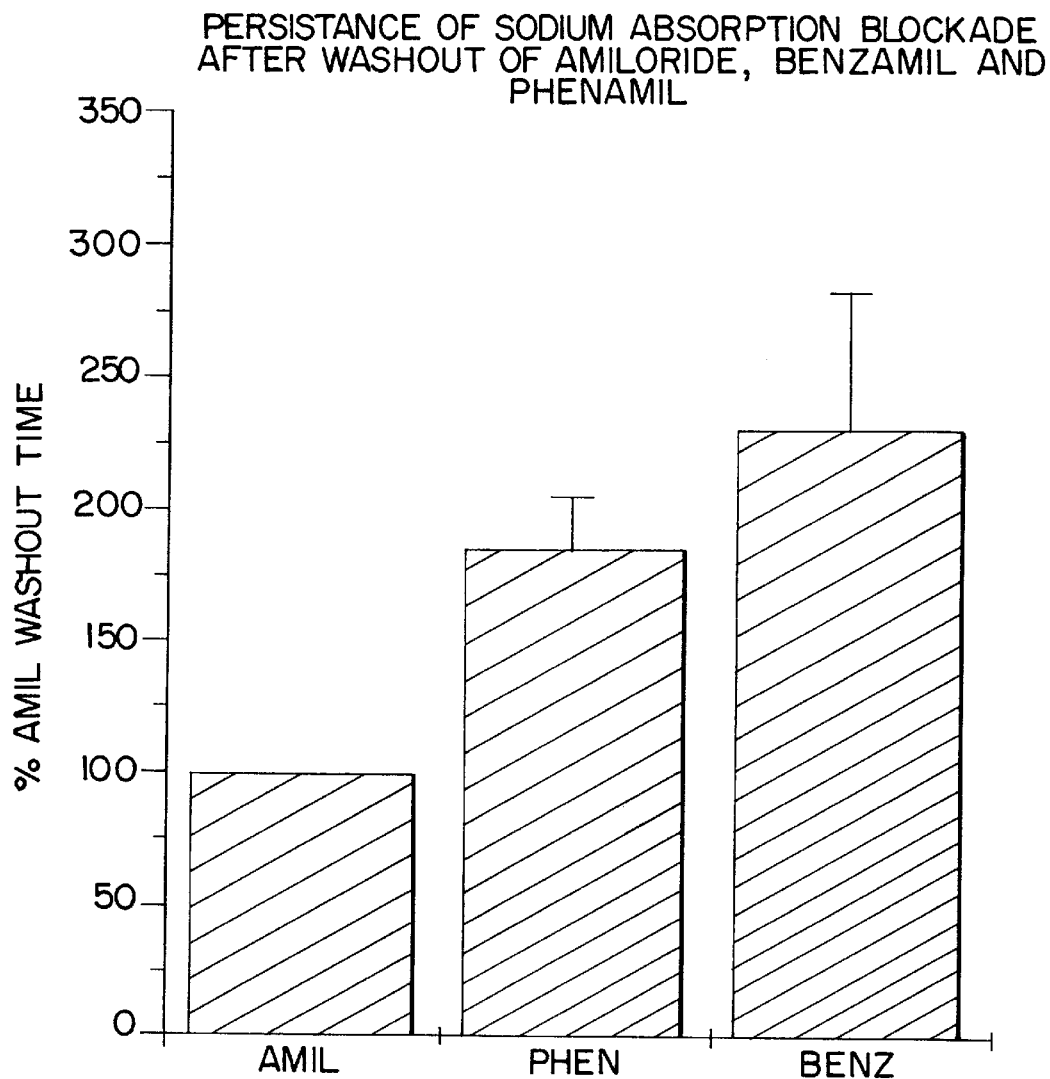
FIG. 2 shows a comparison of the persistence of the $Na^+$ absorption blockade after the washout of amiloride, benzamil and phenamil. The time needed for the washout of phenamil and benzamil as compared to the time needed to wash out amiloride is illustrated.

FIG. 2 illustrates a comparison of the persistence of the $Na^+$ absorption blockade after the washout of amiloride, benzamil and phenamil. The time needed for the washout of phenamil and benzamil as compared to the time needed to wash out amiloride is shown. Benzamil and phenamil have a significantly longer duration of activity than amiloride, with benzamil and phenamil remaining effective in sodium-absorbing channels almost twice as long as amiloride.

The foregoing Examples are illustrative of the present invention, and are not to be construed as limiting thereof. The invention is defined by the following claims, with equivalents of the claims to be included therein.

That which is claimed is:

1. A method of hydrating mucous secretions in the lungs of a subject in need of such treatment, comprising administering benzamil to the lungs of the subject in an amount effective to hydrate lung mucous secretions.

2. A method according to claim 1, wherein said benzamil is administered by delivering an aerosol suspension of respirable particles comprised of benzamil to the lungs of said subject.

3. A method according to claim 2, wherein said particles are selected from the group consisting of solid particles and liquid particles.

4. A method according to claim 2, wherein said aerosol is comprised of particles having a particle size within the range of about 1 to 10 microns.

5. A method according to claim 1, wherein said benzamil is administered in an amount sufficient to achieve concentrations of benzamil on the airway surfaces of said subject of from about $10^{-9}$ to about $10^{-1}$ Moles/liter.

6. A method according to claim 1, further comprising concurrently administering to said subject a compound of Formula (I), or pharmaceutically acceptable salt thereof:

(I)

[Chemical structure of Formula (I)]

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br;

in an amount effective to stimulate chloride secretion into said mucous from respiratory epithelial cells and/or stimulate cilia beat frequency therein.

7. A method of treating cystic fibrosis in a human subject in need of such treatment, comprising administering by inhalation an aerosol suspension of respirable particles to the respiratory system of said subject, said particles comprised of benzamil, said benzamil administered in an amount effective to hydrate retained lung mucous secretions in the lungs of said subject, whereby the retained mucous secretions are more easily transported from the lungs via mucociliary action.

8. A method according to claim 7, wherein said particles are selected from the group consisting of solid particles and liquid particles.

9. A method according to claim 7, wherein said aerosol is comprised of particles having a particle size within the range of about 1 to 10 microns.

10. A method according to claim 7, wherein said benzamil is administered in an amount sufficient to achieve concentrations of benzamil on the airway surfaces of said subject of from about $10^{-9}$ to about $10^{-1}$ Moles/liter.

11. A method according to claim 7, further comprising concurrently administering to said subject a compound of Formula (I), or pharmaceutically acceptable salt thereof:

(I)

[Chemical structure of Formula (I)]

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br;

in an amount effective to stimulate chloride secretion into said mucous from respiratory epithelial cells and/or stimulate cilia beat frequency therein.

12. A method of hydrating mucous secretions in the lungs of a subject in need of such treatment, comprising administering phenamil to the lungs of the subject in an amount effective to hydrate lung mucous secretions.

13. A method according to claim 12, wherein said phenamil is administered by delivering an aerosol suspension of respirable particles comprised of phenamil to the lungs of said subject.

14. A method according to claim 13, wherein said particles are selected from the group consisting of solid particles and liquid particles.

15. A method according to claim 13, wherein said aerosol is comprised of particles having a particle size within the range of about 1 to 10 microns.

16. A method according to claim 12, wherein said phenamil is administered in an amount sufficient to achieve concentrations of phenamil on the airway surfaces of said subject of from about $10^{-9}$ to about $10^{-1}$ Moles/liter.

17. A method according to claim 12, further comprising concurrently administering to said subject a compound of Formula (I), or pharmaceutically acceptable salt thereof:

$$\text{(I)}$$

[Structure of Formula (I): nucleotide triphosphate analog with pyrimidine base bearing R₂ substituent, ribose sugar with two OH groups, and triphosphate chain with X₁, X₂, X₃ substituents and R₁ linker, labeled γ, β, α]

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br;

in an amount effective to stimulate chloride secretion into said mucous from respiratory epithelial cells and/or stimulate cilia beat frequency therein.

18. A method of treating cystic fibrosis in a human subject in need of such treatment, comprising administering by inhalation an aerosol suspension of respirable particles to the respiratory system of said subject, said particles comprised of phenamil, said phenamil administered in an amount effective to hydrate retained lung mucous secretions in the lungs of said subject, whereby the retained mucous secretions are more easily transported from the lungs via mucociliary action.

19. A method according to claim 18, wherein said particles are selected from the group consisting of solid particles and liquid particles.

20. A method according to claim 18, wherein said aerosol is comprised of particles having a particle size within the range of about 1 to 10 microns.

21. A method according to claim 18, wherein said phenamil is administered in an amount sufficient to achieve concentrations of phenamil on the airway surfaces of said subject of from about $10^{-9}$ to about $10^{-1}$ Moles/liter.

22. A method according to claim 18, further comprising concurrently administering to said subject a compound of Formula (I), or pharmaceutically acceptable salt thereof:

$$\text{(I)}$$

[Structure of Formula (I): same nucleotide triphosphate analog as above]

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br;

in an amount effective to stimulate chloride secretion into said mucous from respiratory epithelial cells and/or stimulate cilia beat frequency therein.

* * * * *